Figure 1:
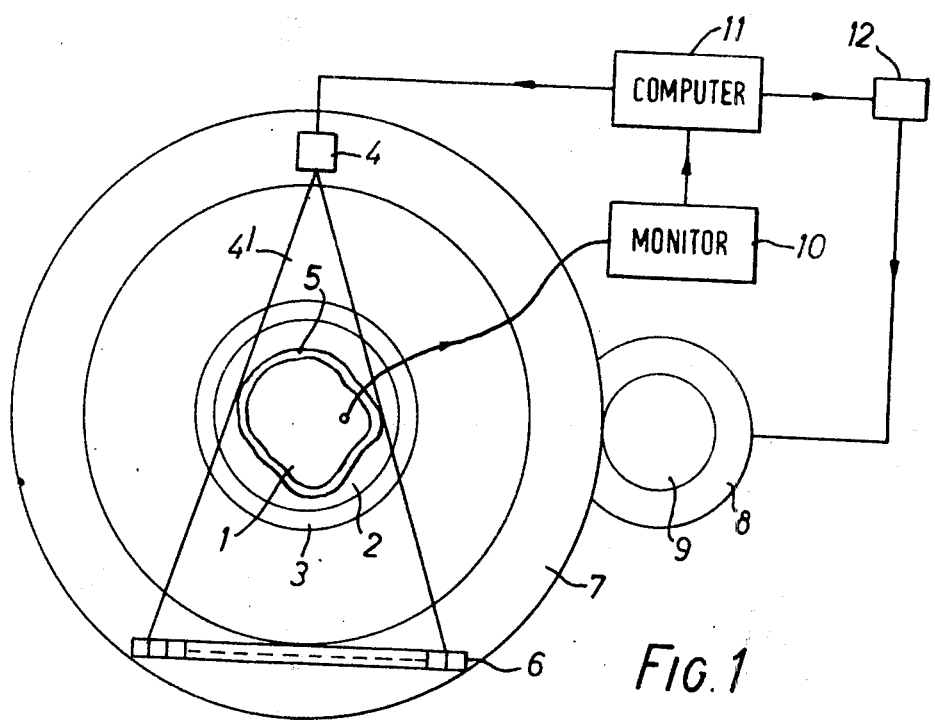

United States Patent [19]
Hounsfield

[11] 3,952,201
[45] Apr. 20, 1976

[54] RADIOGRAPHY

[75] Inventor: Godfrey Newbold Hounsfield, Newark, England

[73] Assignee: EMI Limited, Hayes, England

[22] Filed: July 17, 1974

[21] Appl. No.: 489,142

[30] Foreign Application Priority Data
July 21, 1973 United Kingdom............... 34858/73

[52] U.S. Cl............................... 250/403; 250/402; 250/401; 250/491
[51] Int. Cl.² ........................................ H05G 1/00
[58] Field of Search ........... 250/402, 403, 404, 320, 250/322, 490, 491

[56] References Cited
UNITED STATES PATENTS

| | | | |
|---|---|---|---|
| 2,152,045 | 2/1939 | Gulland .............................. | 250/402 |
| 2,190,389 | 2/1940 | Strauss................................ | 250/322 |
| 3,432,657 | 3/1969 | Slavin ................................. | 250/490 |
| 3,502,877 | 3/1970 | Splain ................................. | 250/403 |
| 3,576,997 | 5/1971 | Slavin ................................. | 250/490 |
| 3,670,163 | 6/1972 | Lajus .................................. | 250/320 |
| 3,825,761 | 7/1974 | Geratsdorfer....................... | 250/402 |
| 3,852,611 | 12/1974 | Cesar.................................. | 250/490 |

*Primary Examiner*—Archie R. Borchelt
*Assistant Examiner*—B. C. Anderson
*Attorney, Agent, or Firm*—Fleit & Jacobson

[57] ABSTRACT

In radiographic apparatus arranged to investigate a region of a body which can include a moving member, for example the heart of a human patient, means are provided for compensating (at least in part) for the blurring of the radiograph which might be caused by the motion of said member. The motion of the member is monitored and used either to periodically interrupt the irradiation of the body each time the motion becomes too great or enable information which might be confused, due to the motion, to be rejected before the radiograph is produced.

7 Claims, 4 Drawing Figures

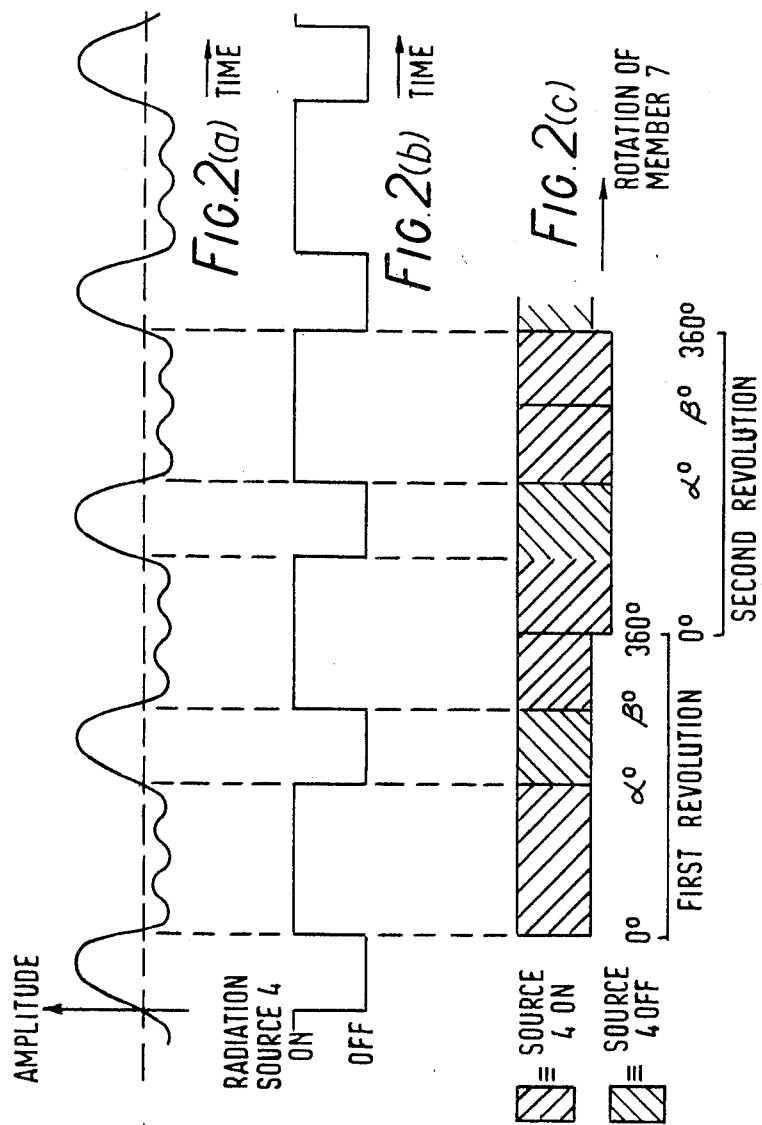

RADIOGRAPHY

The present invention relates to radiography.

In the specification of our British Pat. No. 1,283,915 there is described and claimed a method of, and apparatus for, investigating a body by means of radiation such as X- or γ- radiation. The use of the said method and apparatus enables the production of a representation of a two-dimensional "slice" effectively taken through the body in a plane defined by a plurality of sets of rays directed through the body from a source of such radiation toward detector means disposed at the side of the body remote from the source; the source and the detector means being orbited around the body so as to expose said body to radiation from a plurality of different angular positions around the body.

The representation consists of a matrix of absorption or transmission coefficients appropriate to the elements of a two-dimensional matrix of elements notionally delineated in the aforementioned plane of the body. If the plane contains a member which moves, however, the motion of the member can cause localised blurring of the representation.

Accordingly, it is one object of the invention to provide apparatus for examining a living body by means of penetrating radiation, such as X- or γ- radiation, including source means for irradiating said body with said radiation, scanning means for causing said source means to scan around said body to direct said radiation through said body along a plurality of paths lying in a plane of finite thickness which intersects said body, detector means, adapted to scan with said source means, disposed to receive the radiation emergent from said body along said paths and adapted to provide, in accordance with a prescribed programme, respective output signals indicative of the absorption suffered by said radiation on traversing each of said paths, monitoring means for monitoring the motion of the heart of the body under examination and for producing motion signals indicative of said motion, control means, responsive to said motion signals, for generating a control signal indicative of periods during which said motion exceeds a threshold level, means responsive to said control signal for interrupting said output signals during said periods, further means responsive to said control signal for generating a further control signal for application to said scanning means to control said scan whereby output signals omitted from said programme due to said interruptions are subsequently provided by said detector means.

It is another object of the invention to provide apparatus for examining a living body by means of penetrating radiation, such as X- or γ- radiation, including source means and detector means, disposed on opposite sides of said body, respectively for irradiating said body along a plurality of paths disposed in a plane of finite thickness which is affected by movement of the heart of said body, and for detecting said radiation emergent from said body along each of said paths, scanning means for scanning said source means and said detector means around said body, monitoring means for monitoring the motion of said heart and for providing a motion signal indicative of said motion, means responsive to said motion signal for selecting output signals derived during a selected phase of said motion and means for producing an output representation in response to said signal indicative of the plane of said body when the heart is in said phase.

It is still another object of the invention to provide a method of examining a living body by means of penetrating radiation, such as X- or γ- radiation, including the steps of:

a. monitoring the motion of the heart of said body and providing motion signals indicative of said motion, b. irradiating said body along a plurality of paths disposed in a plane of finite thickness which intersects said body, c. scanning said source means around said body to irradiate said body along other paths in said plane, d. detecting the radiation emergent from the body along each of said paths and providing, in accordance with a prescribed programme, output signals indicative of the absorption suffered by said radiation on traversing said paths, e. operating upon said motion signals to provide
   i. a first control signal indicative of periods during which said motion of said heart is in excess of a prescribed threshold level and
   ii. a further control signal for controlling said scanning, f. interrupting said output signals during said periods by means of said first control signal, and utilising said further control signal to control said scanning such that output signals omitted from said programme due to said interruption are provided at another stage of the scanning.

In order that the invention may be clearly understood and readily carried into effect, one embodiment thereof will now be described with reference to the accompanying drawings of which:

FIG. 1 shows, in schematic plan view and part block diagrammatic form, one example of apparatus in accordance with the present invention, and FIG. 2 shows waveforms explanatory of the operation of the apparatus shown in FIG. 1.

Referring now to the drawings, a body 1 to be examined is surrounded with water 2 which is maintained in a reservoir 3 formed of a plastics material substantially transparent to the radiation produced by a source 4. The body 1 is enclosed in a sheath 5 of flexible, waterproof material such as rubber so as to protect the body from the water. The source 4 produces a sectoral, planar swath of radiation 4[1], and the source and a bank 6 of radiation detectors such as scintillator crystals are mounted on an annular turntable member 7 which is rotatable by means of a variable speed electric motor 8. The motor 8 drives a gear wheel 9 which co-operates with gear teeth provided all around the periphery of the member 7.

Each of the scintillator crystals in the bank 6 is provided with a collimator (not shown) to define the path through the body which radiation incident on the particular crystal has taken. The crystals are such as to provide a light output indicative of the amount of radiation received thereby and the light output of each crystal is fed via a respective light pipe (not shown) to a respective photomultiplier (not shown). The electrical signals produced by the photomultipliers in response to the radiation incident on the various detectors are processed, for example as described in the aforementioned patent specification, in order to produce a representation of the plane of the body which is irradiated by the source 4.

In the event that the said plane of the body intersects the heart, for example, of the patient, an electrocardiogram (e.c.g.) is taken of the patient just prior to the radiographic examination by means of a monitoring and processing circuit 10.

The e.c.g. is typically of the form shown in FIG. 2(a), with each heartbeat being followed by a period of relatively little movement. A threshold is indicated by the horizontal dashed line in FIG. 2 and the e.c.g. is processed in a computing circuit 11 to derive an operating waveform of the form shown in FIG. 2(b) for application to the source 4.

The source 4 conveniently comprises an X-ray tube, for example a rotating anode tube, and the waveform of FIG. 2(b) is adjusted to a suitable amplitude and applied to the grid electrode of the tube so as to inhibit the emission of X-rays each time the amplitude of the heartbeat motion exceeds the aforementioned threshold.

In an alternative technique, the waveform of FIG. 2(b) is applied, suitably modified in shape and amplitude to a deflection coil arrangement (not shown) associated with the tube. In this case the arrangement is such as to cause the electron beam of the tube to be deflected so that it does not strike the anode of the tube each time the heartbeat motion exceeds the threshold.

It will be appreciated that the waveform of FIG. 2(b) need not be used to control the actual emission of radiation by the source 4. Instead, the source 4 could be arranged to emit radiation continuously and a shutter, opaque to said radiation, could be operated in response to the e.c.g. waveform so as to intercept the radiation emitted by the source 4 during the "OFF" periods.

The circuit 11 is also effective to compute the rotational speed for the member 7 which is necessary to ensure that "ON" periods of the radiation source occur, on the or a subsequent rotation of member 7, at angular positions such as $\alpha$-$\beta$ (FIG. 2(c)) from which the body was not irradiated during the first revolution of member 7. This is achieved via a speed control circuit 12 which responds to the computed rotational speed to actuate the motor 8 accordingly. As can be seen from FIG. 2(c), the speed of the member 7 is adjusted so that, on the second revolution of member 7, the source 4 is rendered active during the traversal of the angular region $\alpha$-$\beta$ throughout which region the source was inactive during the first revolution of member 7.

In some circumstances it may not be possible to arrange that the source 4 is rendered active over regions such as $\alpha$-$\beta$ on the second scan, and in such circumstances the speed of the motor 8 is controlled to ensure that the source 4 is rendered active during the region $\alpha$-$\beta$ in the least practicable number of revolutions.

Overlapping information, i.e., information derived from the same angular region during successive scans, can be discarded. Alternatively, instead of obtaining such information and discarding it, the source 4 may be rendered inactive during periods in which it would produce superfluous information.

The monitoring circuit 10 may be maintained in use during the operation of the scanning apparatus so that fluctuations in the heartbeat of the patient during his examination can be detected and compensated for.

As a further alternative, the radiation source 4 need not be rendered inactive when the heart is not stationary. Instead the apparatus may be caused to execute several revolutions around the patient, while the patient's heart is monitored by the circuit 10. All the information from the scanning apparatus and the circuit 10 is then correlated in the computer 11 and any unwanted information (i.e., that obtained when the heart's motion exceeded the threshold level) is rejected. It is still advantageous, however, to monitor the patient's hearbeat rate prior to the examination so that the speed of the motor 8 can be adjusted to a suitable initial value.

What I claim is:

1. Apparatus for examining a living body by means of penetrating radiation, such as X- or $\gamma$- radiation, including source means for irradiating said body with said radiation, scanning means for causing said source means to scan around said body to direct said radiation through said body along a plurality of paths lying in a plane of finite thickness which intersects said body, detector means, adapted to scan with said source means, disposed to receive the radiation emergent from said body along said paths and adapted to provide, in accordance with a prescribed programme, respective output signals indicative of the absorption suffered by said radiation on traversing each of said paths, monitoring means for monitoring the motion of the heart of the body under examination and for producing motion signals indicative of said motion, control means, responsive to said motion signals, for generating a control signal indicative of periods during which said motion exceeds a threshold level, means responsive to said control signal for interrupting said output signals during said periods, further means responsive to said control signal for generating a further control signal for application to said scanning means to control said scan whereby output signals omitted from said programme due to said interruption are subsequently provided by said detector means.

2. Apparatus according to claim 1 wherein said source means is arranged to produce a substantially planar, sectoral shaped beam of said radiation and said detector means comprises a plurality of detector devices.

3. Apparatus according to claim 1 wherein said scanning means is adapted to orbit the source means and the detector means around the body, about an axis passing through said body in a direction substantially perpendicular to the plane of said paths.

4. Apparatus according to claim 1, wherein said source means comprises an X-ray tube, including means for applying said first mentioned control signal to a modulator electrode of said tube so as to inhibit the production of said radiation during said periods.

5. Apparatus according to claim 1, wherein said source means comprises an X-ray tube, including deflection coil means associated with said tube and adapted to receive said first mentioned control signal and to respond thereto to deflect the electron beam of said tube away from the X-ray producing anode thereof during said periods.

6. Apparatus for examining a living body by means of penetrating radiation, such as X- or $\gamma$- radiation, including source means and detector means, disposed on opposite sides of said body, respectively for irradiating said body along a plurality of paths disposed in a plane of finite thickness which is affected by movement of the heart of said body, and for detecting said radiation emergent from said body along each of said paths, scanning means for scanning said source means and said detector means around said body, monitoring means for monitoring the motion of said heart and for providing a motion signal indicative of said motion, means responsive to said motion signal for selecting output signals derived during a selected phase of said motion and means for producing an output representation in response to said signal indicative of the plane of said body when the heart is in said phase.

7. A method of examining a living body by means of penetrating radiation, such as X- or γ- radiation, including the steps of:
 a. monitoring the motion of the heart of said body and providing motion signals indicative of said motion,
 b. irradiating said body along a plurality of paths disposed in a plane of finite thickness which intersects said body,
 c. scanning said source means around said body to irradiate said body along other paths in said plane,
 d. detecting the radiation emergent from the body along each of said paths and providing, in accordance with a prescribed programme, output signals indicative of the absorption suffered by said radiation on traversing said paths,
 e. operating upon said motion signals to provide
  i. a first control signal indicative of periods during which said motion of said heart is in excess of a prescribed threshold level and
  ii. a further control signal for controlling said scanning,
 f. interrupting said output signals during said periods by means of said first control signal, and utilizing said further control signal to control said scanning such that output signals omitted from said programme due to said interruption are provided at another stage of the scanning.

* * * * *